US011459598B2

United States Patent
MacKenzie et al.

(10) Patent No.: US 11,459,598 B2
(45) Date of Patent: Oct. 4, 2022

(54) MULTIPLEX DNA IMMUNO-SANDWICH ASSAY (MDISA)

(71) Applicant: Quateris LLC, Belmont, MA (US)

(72) Inventors: Malcolm MacKenzie, Belmont, MA (US); Ilya Alexandrov, Natick, MA (US); Michael Sherman, Maale Adumim (IL)

(73) Assignee: Quateris LLC, Newton, MA (US)

( * ) Notice: Subject to any disclaimer, the term of this patent is extended or adjusted under 35 U.S.C. 154(b) by 343 days.

(21) Appl. No.: 15/768,868

(22) PCT Filed: Oct. 20, 2016

(86) PCT No.: PCT/US2016/057853
§ 371 (c)(1),
(2) Date: Apr. 17, 2018

(87) PCT Pub. No.: WO2017/070309
PCT Pub. Date: Apr. 27, 2017

(65) Prior Publication Data
US 2019/0276875 A1    Sep. 12, 2019

Related U.S. Application Data (60) Provisional application No. 62/243,682, filed on Oct. 20, 2015.

(51) Int. Cl.
*C12Q 1/6804* (2018.01)

(52) U.S. Cl.
CPC .................................. *C12Q 1/6804* (2013.01)

(58) Field of Classification Search
CPC ............................. C12Q 1/6816; C12Q 1/6804
See application file for complete search history.

(56) References Cited

U.S. PATENT DOCUMENTS

| | | | |
|---|---|---|---|
| 2007/0026430 A1 | 2/2007 | Andersen | |
| 2008/0008997 A1 | 1/2008 | Levy | |
| 2010/0240101 A1 | 9/2010 | Lieberman | |
| 2012/0277113 A1 | 11/2012 | Huang | |
| 2013/0011833 A1* | 1/2013 | Quake | C12Q 1/6804 435/6.11 |
| 2013/0288249 A1* | 10/2013 | Gullberg | C12Q 1/6804 435/6.11 |
| 2014/0194311 A1 | 7/2014 | Gullberg | |

FOREIGN PATENT DOCUMENTS

| | | |
|---|---|---|
| WO | WO 2001/061037 | 8/2001 |
| WO | WO 2004/094456 | 11/2004 |
| WO | WO 2005/123963 | 12/2005 |
| WO | WO 2012/049316 | 4/2012 |
| WO | WO 2014/076214 | 5/2014 |

OTHER PUBLICATIONS

James Flanigon, et al., Multiplex Protein Detection with DNA Readout via Mass Spectrometry, N Biotechnol., Jan. 25, 2013, 30(2): 153-158.*
Flanigon, Multiplex protein detection with DNA readout via mass spectrometry, N Biotechnol, Jan. 25, 2013; 30(2): 153-158, Supplementary Materials. (Year: 2013).*
Flanigon, Multiplex protein detection with DNA readout via mass spectrometry, N Biotechnol, Jan. 25, 2013; 30(2): 153-158, Table S-2 (Year: 2013).*
Adler, Sensitivity by combination: immuno-PCR and related technologies, Analyst, 133:702-718, 2008. (Year: 2008).*
Flanigon, Multiplex Detection with DNA Readout via Mass Spectrometry, new Biotechnoly, vol. 30, No. 2, pp. 153-158, 2013.
International Search Report from WO 2017/070309.
Written Opinion from WO 2017/070309.

* cited by examiner

*Primary Examiner* — Gary Benzion
*Assistant Examiner* — Carolyn L Greene
(74) *Attorney, Agent, or Firm* — Patent GC; Naomi S. Biswas (57) ABSTRACT

This invention is directed to a method for detecting near and distant interactions between cells, organelles and other large structures. This method can also be used for specific detection and quantification of Antibody or other binding moiety protein-protein and macro-molecular interactions, as well as quantitative analysis of multiple proteins and their modifications.

19 Claims, 8 Drawing Sheets

Specification includes a Sequence Listing.

Figure 1

Option 1

Figure 4

Example of an AOT conjugated to the antibody

*Antibody oligo tags can also consist only of ABSS sequences – common sequence is optional.

Figure 5: Example 1

SEQUENCE LISTING

<160> NUMBER OF SEQ ID NOS: 5

<210> SEQ ID NO 1
<211> LENGTH: 22
<212> TYPE: DNA
<213> ORGANISM: Artificial sequence
<220> FEATURE:
<223> OTHER INFORMATION: Tag

<400> SEQUENCE: 1
gatgcggata gcgaagatag ct                                    22

<210> SEQ ID NO 2
<211> LENGTH: 23
<212> TYPE: DNA
<213> ORGANISM: Artificial sequence
<220> FEATURE:
<223> OTHER INFORMATION: Tag

<400> SEQUENCE: 2
gtctagtcta tgtgctcagc gag                                   23

<210> SEQ ID NO 3
<211> LENGTH: 16
<212> TYPE: DNA
<213> ORGANISM: Artificial sequence
<220> FEATURE:
<223> OTHER INFORMATION: Signature sequence

<400> SEQUENCE: 3
agcacaacat tgcaga                                           16

<210> SEQ ID NO 4
<211> LENGTH: 16
<212> TYPE: DNA
<213> ORGANISM: Artificial sequence
<220> FEATURE:
<223> OTHER INFORMATION: Signature sequence

<400> SEQUENCE: 4
gttacaacac gatcct                                           16

<210> SEQ ID NO 5
<211> LENGTH: 28
<212> TYPE: DNA
<213> ORGANISM: Artificial sequence
<220> FEATURE:
<223> OTHER INFORMATION: Adapter-Insert

<400> SEQUENCE: 5
gtcgtgactg ggaaaaccct ggcgtctg                              28

MULTIPLEX DNA IMMUNO-SANDWICH ASSAY (MDISA)

CROSS-REFERENCE TO RELATED APPLICATIONS

This application claims priority to provisional application U.S. Ser. No. 62/243,682, filed Oct. 20, 2015, which is incorporated herein by reference.

FIELD OF THE INVENTION

This invention is directed to methods for detecting near and distant interactions between cells, organelles and other large structures, and compounds used in the assay. The compounds and methods can also be used for specific detection and quantification of protein-protein and macro-molecular interactions, as well as quantitative analysis of multiple proteins and their modifications. More specifically, analyte detection is achieved in the present multiplex DNA immuno-sandwich assay (MDISA) by tagging pairs of antibodies with antibody oligo tags wherein such antibody oligo tags cannot bind or ligate to each other, ligating an adapter insert between the two antibody oligo tags, cleaving the joint adapter insert and oligo tags from the antibody pair, amplifying the cleaved joint adapter insert and antibody oligo tags, and detecting the amplification product. With the adapter insert providing length between the antibody pair, the method provides a means of detecting distant interactions.

BACKGROUND OF THE INVENTION

The present method is used to detect distant interactions including interactions between cells, organelles and other large structures. It also can be used for detection and quantification of protein-protein and protein-nucleic acid interactions in cells and solutions. The method is significantly more sensitive than the current methods, such as a Western Blot. The assay of the present invention provides additional efficiencies over prior art assays since it can be performed in a high-throughput manner, and can be easily performed in a 96-well format and automated. One advantage of the present method is that it can be done in a multiplex format and can detect multiple interactions in a single sample. Another advantage of the present invention is the inclusion of the adapter-insert, which provides length between the antibody pairs in order to detect distant interactions or large protein complexes. The length of the adapter insert can vary and can be specifically set for the distance of the interactions to be evaluated. The presence of this adapter insert is an advantage over prior known detection assays.

SUMMARY OF THE INVENTION

The present invention is directed to methods for detecting interactions between cells, organelles and other large structures, and to compounds used in the assay. The compounds and methods of the present invention can also be used for specific detection and quantification of protein-protein and macro-molecular interactions, as well as quantitative analysis of multiple proteins and their modifications.

In one embodiment, the invention is directed to compounds and methods for detecting analytes and association between analytes in a sample, the method comprising incubating the sample with at least two analyte-binding moieties that carry DNA oligo tags specific for each binding moiety, wherein the analyte binding moieties are not able to ligate to each other, adding an adapter-insert DNA molecule, wherein the opposing ends of the adapter-insert DNA molecule can ligate to the DNA oligo tags of the binding moieties; adding a ligase, resulting in a ligated single DNA Product comprised of the DNA oligo tags and the adapter-insert DNA molecule, attached to the analyte-binding moieties, amplifying DNA sequences corresponding to the DNA oligo tags, or portions thereof; and analyzing the amplified DNA sequences to detect analytes and associations between analytes by sequence analysis.

Any mode of sequence detection and analysis that enables quantification that is known in the art can be used. In a preferred embodiment the analytical method used is Next Generation Sequencing (NGS). In one embodiment, prior to amplifying and sequencing, the ligated DNA Product, or a portion thereof, is detached from the binding moieties, and the DNA Product, or a portion thereof, is self-ligated, wherein the DNA oligo tags, or portions of thereof, are located in proximity to each other, and then the self-ligated DNA sequence is amplified. In another embodiment, portions of the ligated DNA Product are amplified and sequenced without detachment and re-ligation.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

BRIEF DESCRIPTION OF THE DRAWINGS

FIGS. 6A-F illustrates use of the MDISA method to detect several proteins of interest. To define sensitivity and dynamic range of the assay, cell lysate was titrated in the range between 0.6 ng and 150 ng and measured the content for several selected targets. As seen in the FIGS. 6A-6F, in most cases there is a clear linearity in the range between 5.6 ng to 150 ng and for some targets the dynamic range is even wider. In the graphs in FIGS. 6A-6F, the Y-axis is the relative amount of DNA product. The samples are relative to the 150 ng datapoint, which is equal to 1.

DETAILED DESCRIPTION OF THE INVENTION

As used throughout the disclosure, the following terms, unless otherwise indicated, shall be understood to have the following meanings.

Definitions

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "cell" as used herein refers to the smallest structural and functional unit of an organism. Microscopic organisms typically consist of a single cell, which is either eukaryotic or prokaryotic.

The term "subcellular structure" as used herein refers to any structure contained within a cell. Subcellular structures are individual components of a cell that when put together form a complete cell. Examples of subcellular structures are organelles, including Golgi apparatus, smooth and rough endoplasmic reticulum, nucleus and mitochondria.

"Nucleic acid sequence" and "nucleotide sequence" as used herein refer to an oligonucleotide or polynucleotide, and fragments or portions thereof, and to DNA, RNA, or LNA of genomic or synthetic origin which may be single- or double-stranded, and represent the sense or antisense strand.

The terms "oligonucleotide" and "oligo" as used herein, are interchangeable, and refer to short double stranded DNA, RNA, LNA or other types of nucleic acid molecules.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked by an immunogen (antigen). It is desired that the antibody demonstrates specificity to epitopes contained in the immunogen.

The terms "specific affinity", "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample" as used herein, is used in its broadest sense and includes environmental and biological samples. Environmental samples include material from the environment such as soil and water. Biological samples may be animal, including, human, fluid (e.g., nasopharyngeal discharge, blood, plasma and serum), solid (e.g., stool), tissue, cultured cells, liquid foods (e.g., milk), and solid foods (e.g., vegetables). For example, a pulmonary sample may be collected by bronchoalveolar lavage (BAL) which comprises fluid and cells derived from lung tissues. A biological sample may be collected that is suspected of containing a virus-infected cell, tissue extract, or body fluid.

Applications of the Assay

The present invention is directed to methods for detecting targets and for detecting near and distant interactions between and within cells, organelles and other large structures, and to compounds for use in the assay. This method can also be used for specific detection and quantification of protein-protein and macro-molecular interactions, as well as quantitative analysis of multiple proteins and their modifications.

In one embodiment, the present method is used to detect protein-protein interactions in an isolated protein complex or inside a cell. The method is significantly more sensitive than the current methods, such as a Western Blot. In other embodiments, the present method is used to detect protein expression, protein modifications, protein cleavage, protein phosphorylation, chemical modifications of proteins, and conformational changes in proteins, or anything else that can be detected by antibodies.

The present method can be used to analyze a variety of different material types. In one embodiment, the assay can be used for profiling of tissue samples from patients (including tumor biopsies) and animals. In another embodiment, the assay can be used for analyzing cells in culture, blood, plasma, cell lysates, fine needle biopsies, micro-dialysis fluid, cell culture media, dried blood spots, synovial fluid, cerebrospinal fluid, plaque extract, saliva, or other bodily fluids. In another embodiment, the present method can be used for detecting proteins and their complexes in frozen or FFPE samples. In one embodiment, the assay can be performed on intact fixed cells.

The present method can be used to determine the amounts of proteins complexed together, for example a complex of proteins A and B. The amounts of the complexes present can be compared across different samples. In other embodiments, the present method can be used to determine the presence or absence of multiple proteins in a single sample.

High Throughput

The assay of the present invention provides efficiencies over prior art assays since it can be performed in a high-throughput manner, and can be easily performed in a 96-well format and automated. One advantage of the present method is that it can be done in a multiplex format to detect multiple analytes simultaneously. Antibodies against multiple analytes can be combined in one mix to detect multiple analytes in one sample. The number of antibodies to be combined in one mix can be any number 2 or greater, since the antibodies are used in pairs. In preferred embodiments, the number of antibodies to be combined in one mix can be 50 or greater, 100 or greater, 140 or greater, 192 or greater, 200 or greater, 300 or greater, 400 or greater, 500 or greater, 1,000 or greater, or 2,000 or greater. In a preferred embodiment, 140 antibodies are combined in one mix. In another preferred embodiment 192 antibodies are combined in one mix. The number of analytes to be detected in one mix is limited only by the detection method used. A variety of detection methods can be used, including any detection methods known in the art. Exemplary detection methods include next generation sequencing ("NGS"), qPCR, digital PCR, branching DNA detection methods, and any other type of quantitative or non-quantitative DNA detection methods. In order for the best accuracy of readout of the assay, the number of reads in the next generation sequencing detection approach can range from $1\times10^3$ to $1\times10^5$ per antibody pair, with a preferred range between 1 to $3\times10^4$ per antibody pair. Thus, in a preferred embodiment with a mix containing 70 antibody pairs, these antibody pairs would take up about 1 to $3\times10^6$ reads per sample. Depending on the NGS platform used, such as Illumina or Ion Torrent platforms, multiple samples can be combined in one run. Alternatively, one can use the Biomark qPCR platform from Fluidigm as a detection method for MDISA, which gives the option to detect up to 96 data points in 96 samples. In this case the mix can contain between 2 and 192 antibodies, if two antibodies are used per target.

Analytes

The targets to be detected in the method of the present invention are also referred to herein as analytes. Single or multiple analytes can be detected, and in some embodiments the analytes are present in a mixture. The analytes can be any cellular component or sub-cellular structure, including, but not limited to, proteins (either individual or in complexes), part of a cellular or tissue sample, or any biological fluid. The analytes can also be protein modifications or DNA/RNA modifications. In the method of the present invention, the analyte can be bound to a solid support.

Exemplary proteins to be targeted include, but are not limited to, enzymes, growth factors, cell signaling proteins, transmembrane proteins, ligand-binding proteins, kinases, including but not limited to cyclin-dependent kinases, serine/threonine-specific protein kinases, AMP-activated protein kinase, mitogen-activated protein kinase, focal adhesion kinase, c-Jun N-terminal kinase, interleukin-1 receptor-associated kinase, receptor tyrosine kinases, glycoproteins, cyclin-dependent kinase inhibitors, tubulins, cadherins, docking proteins, transcriptional regulators, such as yes-associated proteins, and any other type of protein. Specific examples of proteins which can be used as analytes for the antibody pairs to target include, but are not limited to, Akt, CD44, Wafl/Cip1, Gsk, Cat, caspase, parp, SQSTM1, cyclin, Ck2, H2AX, p53, EGFR, cadherin, Myc, Socs3, calnexin, PDI, BiP, Chop, Her2, Gli1, Yap1, KJak2, Stat3, Stat5, MEK1, MAPK, Pak1, mTOR, RSK, EBP1, AMPK, NF-kB, IkBalpha, Numb, IRAK4, IKKalpha/beta, cleaved notch, PLCy1, Lck, cAb1, Zap70, Syk, Cofilin, FAK, Src, Hsp40, Hsp70, Hsp27, JNK, smad1, cKit, VEGFR2, IGF1R, MET, PDGFR beta, IRS1, Her3/erB3, c-CBL, TCF-1, a tubulin, Gapdh, and b tubulin. The analytes to be detected can also be protein or DNA/RNA modifications, such as DNA and RNA methylation.

The analytes to be detected can be present in cellular or tissue samples, such as cell culture, tumor biopsies, other pathology samples from subjects, including humans and animals. The analytes to be detected can also be present in any biological fluids, including, but not limited to blood, plasma, cell lysates, fine needle biopsies, micro-dialysis fluid, cell culture media, dried blood spots, synovial fluid, cerebrospinal fluid, plaque extract, saliva, urine, or other bodily fluids. In other embodiments, the analytes to be detected can be present in frozen or FFPE samples. In one embodiment, the assay can be performed on intact fixed cells. The analytes to be detected can be from any organism, including bacteria, fungi, humans, plants, or animals.

Compounds Used to Target the Analytes

For detecting more distant or proximate interactions between proteins or large structures, pairs of antibodies, or other binding moieties, are used, one antibody or other binding moiety for each protein or other analyte. For binding moieties besides antibodies, this approach can work with any Fab fragments, any derivatives of antibody display libraries, antibody display library particles themselves, single chain antibodies, modifications of recombinant antibodies or their fragments, aptamers and alternative scaffolds, as well as other interacting molecules that can be conjugated/fused to an oligo tag. In a preferred embodiment, the binding moiety is an antibody. When the term antibody is used in this description, it is understood that the term antibody can also refer to any of the other binding moieties described herein. In certain embodiments, the binding moieties of the present invention can be primary antibodies, secondary antibodies, or a combination of primary and secondary antibodies. Primary antibodies bind to antigens or proteins directly and secondary antibodies target another (primary) antibody that is bound to an antigen or protein.

Figure 4:
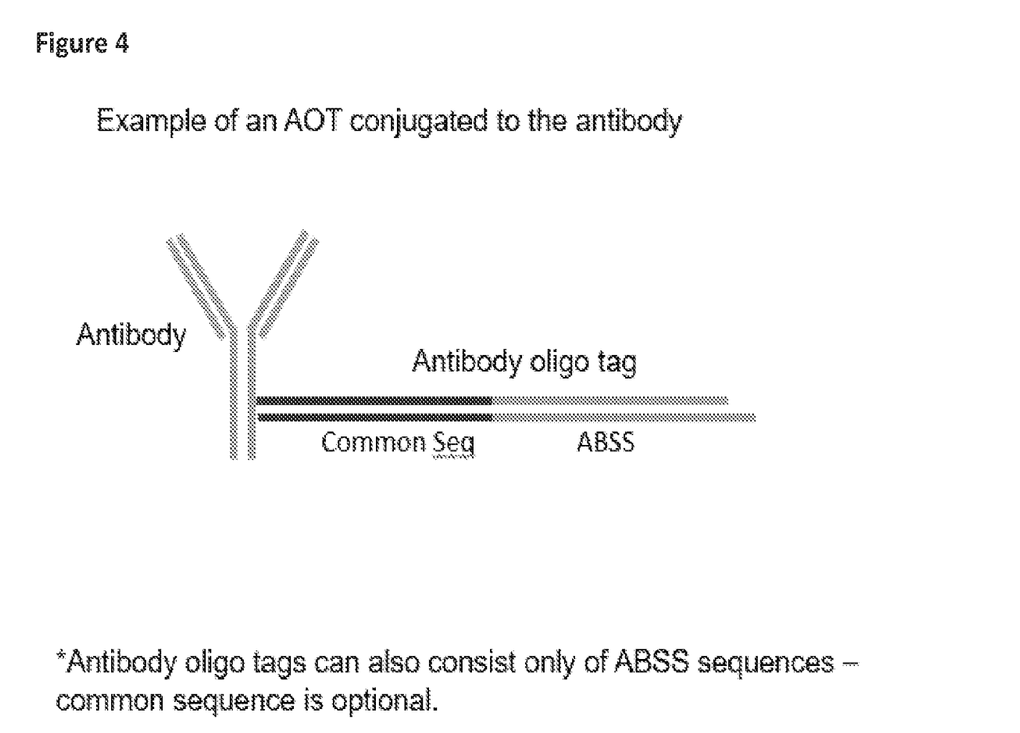
FIG. 4 illustrates an antibody oligo tag conjugated to an antibody.

Each antibody that is used in this assay is tagged with an antibody oligo tag ("AOT"). Each AOT contains an antibody signature sequence ("ABSS") and may optionally contain one of two types of common sequences. If the common sequences are included, they are located at the proximal ends of the AOTs which are conjugated to the antibodies. The ABSSs follow the common sequences and are therefore located at the distal end of the AOT. Common sequences can be optionally integrated into the design of the AOT. It is possible to use any nucleic acid (DNA, RNA, LNA, etc.) as the common sequence. In preferred embodiments, the common sequences are double-stranded DNA sequences. Common sequences can include different integrated elements, including, but not limited to, a restriction enzyme site. Common sequences may also act as a backbone for the AOT. They can also be used to amplify the ABSSs of DNA Products after the AOT's ligation takes place. If the common sequences are not included, then the ABSS is directly conjugated to the antibody. The composition of the AOTs is illustrated in FIG. 4. AOTs can be conjugated to their antibodies by any conjugation methods known in the art. In one embodiment, AOTs are conjugated to the corresponding antibodies by an amine-to-sulfhydryl crosslinker-based conjugation procedure between the AOT and the antibody. In other embodiments, other conjugation procedures use sulfhydryl groups, primary amine groups or carbohydrates on the antibody molecules.

Figure 1:
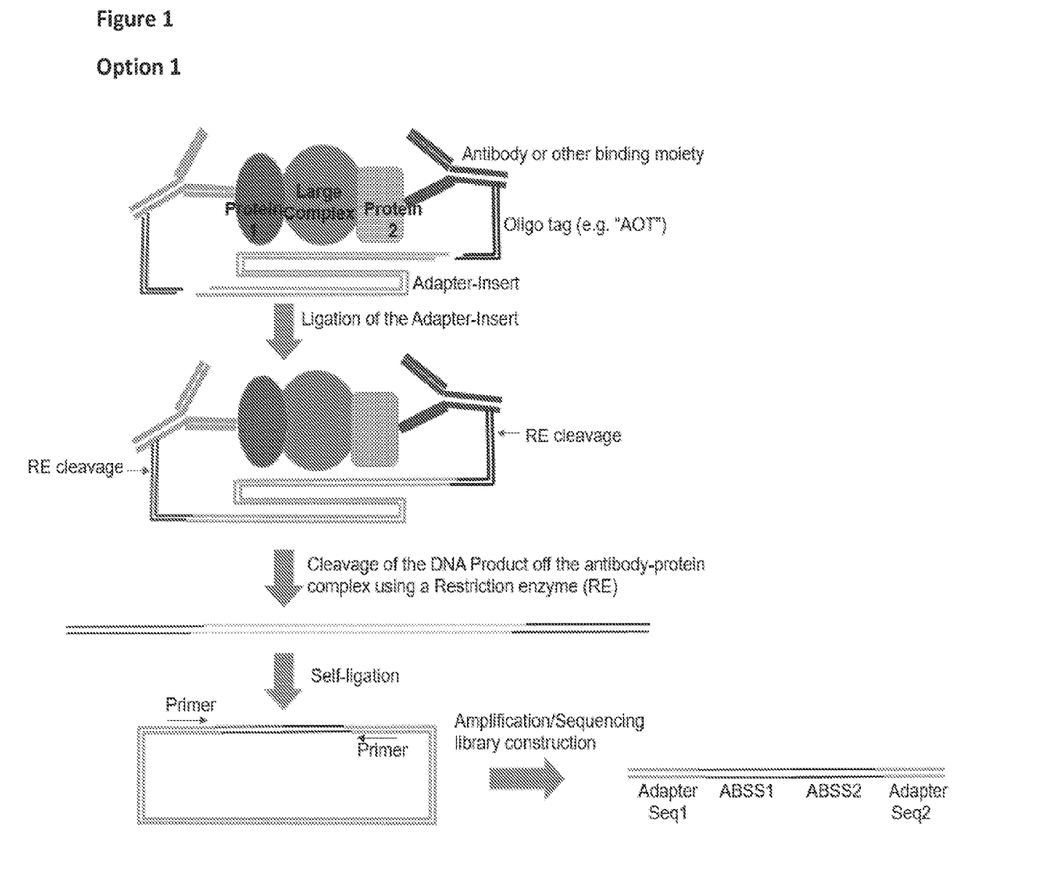
FIG. 1 is a flowchart illustrating the compounds and methods of the present invention for detecting distant interactions between or within large complexes. This figure illustrates a long DNA Product that is cleaved off the antibody-protein complex and is subsequently self-ligated prior to amplification.
Figure 2:
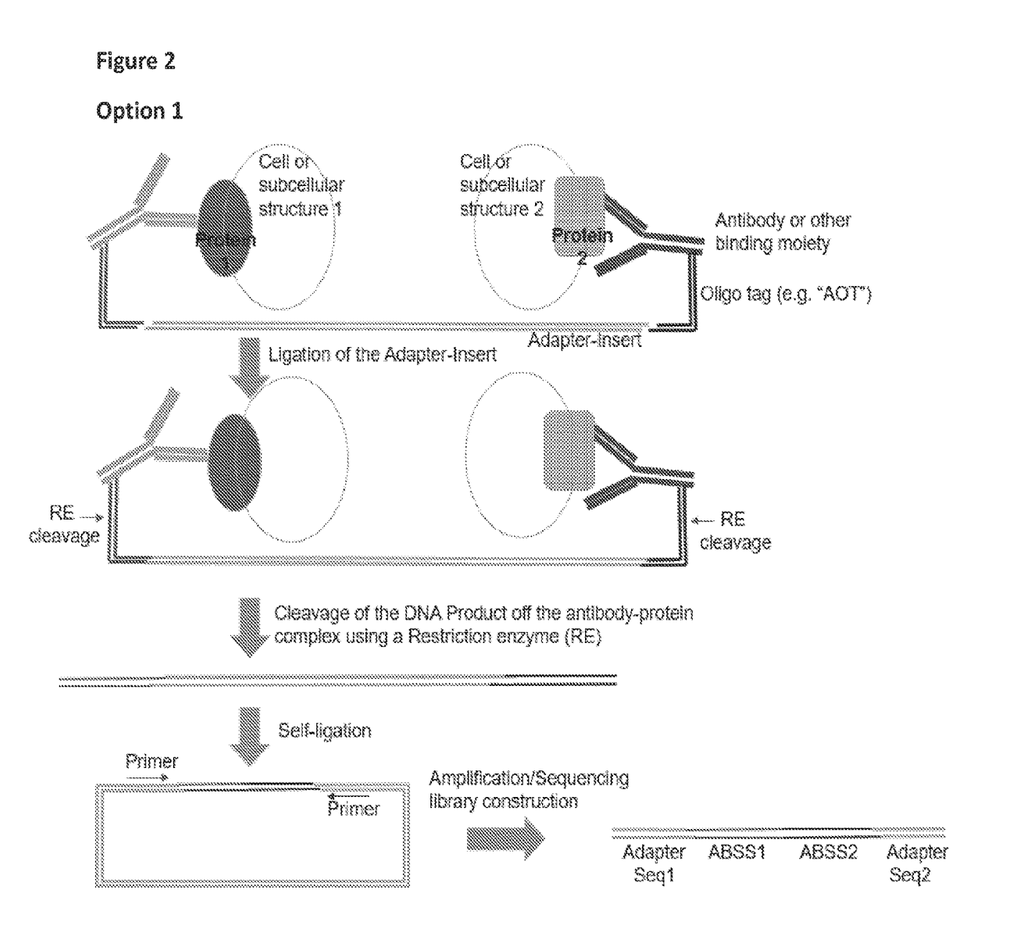
FIG. 2 is a flowchart illustrating the compounds and methods of the present invention for detecting distant interactions, including quantitating cell-cell interactions, and measuring distances between organelles and cell sub-structures. This figure illustrates a long DNA Product that is cleaved off the antibody-protein complex and is subsequently self-ligated prior to amplification.

The ABSS is a specific signature sequence, which contains a specific bar-code, individual for each antibody. It is possible to use any nucleic acid (DNA, RNA, LNA, etc.) as the ABSS sequence. In preferred embodiments, the ABSS is a double-stranded DNA sequence. In addition to an ABSS, each AOT, also may contain one of two types of common sequences. If common sequences are included in the AOTs, then one antibody in each antibody pair (Ab1) is tagged with an AOT containing common sequence 1 and the other antibody in the pair (Ab2) is tagged with an AOT containing common sequence 2. In embodiments of AOTs which include common sequences, the common sequences are at the proximal end of the AOT and are attached to the antibody, and the ABSSs are at the distal end of the AOT in relation to the common sequence. The AOTs are designed in such a way that the ABSSs at their distal ends are not able to ligate or to bind with each other. In some embodiments, as shown in FIGS. 1 and 2, self-ligation occurs between the two AOTs only when each AOT is treated with a restriction enzyme (RE) that cuts the AOTs from the antibodies and frees up the ends of the AOTs that were proximal to the antibody. In these embodiments, the proximal ends of the AOTs bind and ligate to each other in the self-ligation options, as shown in FIGS. 1 and 2.

The AOTs can be of varying lengths. In preferred embodiments, the length of the AOTs ranges from about 10-200 bp, preferably between about 12 bp to 100 bp, and more preferably between about 20-50 bp. The ABSS and common sequences are each preferably DNA sequences, each are preferably between about 5-100 bp, more preferably between about 10-50 bp, and most preferably between about 15 bp and 30 bp. Each ABSS and common sequence have the following preferred characteristics: 50% GC content, unique non-genomic sequence that can be used for amplification by PCR, that will give only one product, and that will have low probability of hairpin structures, selfdimers and heterodimers with its counterpart on the second AOT from the pair. Representative common sequences include common sequence 1 GATGCGGATAGCGAAGATAGCT (SEQ ID NO 1) and common sequence 2 GTCTAGTCTATGTGCTCAGCGAG (SEQ ID NO 2). Representative ABSSs include ABSS 1 AGCACAACATTGCAGA (SEQ ID NO 3) and ABSS 2 GTTACAACACGATCCT (SEQ ID NO 4).

Such tagged antibodies for any number of targets are mixed together and mixed with a sample to be analyzed for the targets. An adapter-insert is added to the mix at this or a later stage ("Adapter-Insert"). It is possible to use any nucleic acids (DNA, RNA, LNA, etc.) as an Adapter-Insert. In a preferred embodiment, the nucleic acid for the Adapter-Insert is double-stranded DNA. The Adapter-Insert is designed to interact with the distal end of AOT on Ab1 at one end and the distal end of AOT on Ab2 at the opposing end. Other embodiments of Adapter-Inserts include double-stranded DNA sequences with preferred length between about 12 and 500 bp, which have the following preferred characteristics: 50% GC content, unique non-genomic sequence that will have low probability of hairpin structures and self-dimers. On the sticky end of the DNA oligo (the distal end) there is a sticky area, usually of 1 to 5 nucleotides, but it could be longer. The sticky ends of the AOTs in the pair have different sequences and thus cannot ligate to each other directly. The Adapter-Insert is designed in such a way so it has the sequences on each side to specifically interact with the two AOTs in the pair. One representative example of an adapter insert is the following sequence: GTCGTGACTGGGAAAACCCTGGCGTCTG (SEQ ID NO 5).

The antibody pairs bind to their respective targets. The Adapter-Insert is added to the mix together with a ligase. Ab1 and Ab2 AOTs are ligated to the same Adapter-Insert in such a way that one end of the Adapter-Insert is being fused to the distal end of the AOT attached to one of the antibodies in the pair (Ab1) and the other end of the Adapter-Insert is being fused to the distal end of the AOT attached to the other antibody in the pair (Ab2). The Adapter-Insert can be i) common for all antibody pairs; ii) specific for a sub-set of antibody pairs; or iii) specific for each antibody pair. It is possible to use any nucleic acids (DNA, RNA, LNA, etc.) as an Adapter-Insert, and as the AOTs. In a preferred embodiment, the nucleic acid for the Adapter-Insert, and the AOTs, is double-stranded DNA. The combination of the AOT for Ab1, the Adapter-Insert, and the AOT for Ab2 is the DNA Product. When the term DNA Product is used in this description, it is understood that DNA Product can comprise any type of nucleic acids, including DNA, RNA, LNA, or any type of nucleic acid polymer.

In certain embodiments, versatility is added to the present assay by using both primary and secondary antibodies. These antibodies can be from any species, including but not limited to mouse, rabbit, rat, goat, recombinant human, or any other known types of antibodies. The primary antibodies should be from different species, such that the secondary antibodies would bind only to its intended primary antibody and do not cross-react. In this embodiment, a pair of primary antibodies can be used together with a pair of secondary antibodies, wherein the secondary antibodies are tagged with AOTs. In additional embodiments, two pairs of primary antibodies can be used together with two pairs of secondary antibodies, such that 4 primary antibodies and 4 secondary antibodies are used. In such embodiments, all 4 primary antibodies are from different species, and the secondary antibodies are produced from a species different than any of the primary antibodies. As an exemplary embodiment, the 4 primary antibodies could each be from mouse, rabbit, rat, and recombinant human, with the secondary antibodies produced in goat.

As an example of an embodiment with a pair of primary and a pair of secondary antibodies, one antibody in the secondary pair could be an anti-rabbit secondary antibody (such as Cat #111-005-003 Jackson Labs) and the second antibody in this pair could be an anti-mouse secondary antibody (such as Cat #115-005-008 Jackson Labs). In this embodiment, this secondary antibody pair can be used in combination with any primary antibody pair where one of the primary antibodies is a rabbit antibody and the second is a mouse antibody. The selected primary antibody pair is chosen to specifically bind to two target proteins in the same or different complexes. The secondary antibodies pair will then bind to that primary antibody pair (the anti-mouse secondary to the mouse primary; the anti-rabbit secondary to the rabbit primary), and thus can be successfully used to detect the two target proteins in the same complex in solution or directly in fixed cells, using MDISA, see Example 1.

This tagged secondary antibody pair can further be used with any primary antibody pair, provided that the primary antibodies are from different species, e.g. one raised in rabbit and another in mouse. A significant benefit of this approach is that the operator is required to perform conjugation only once, and can then use this same conjugated secondary antibody pair on any primary antibody pair (that are from different species). Since the conjugation procedure requires significant amounts of antibody in a purified format, this option has significant economic value. This approach is also useful where securing adequate quantities of the primary antibodies and in the right buffer is not possible. Further, this approach using MDISA is significantly more sensitive than most alternative approaches, and provides for quantification rather than just qualification.

Figure 3:
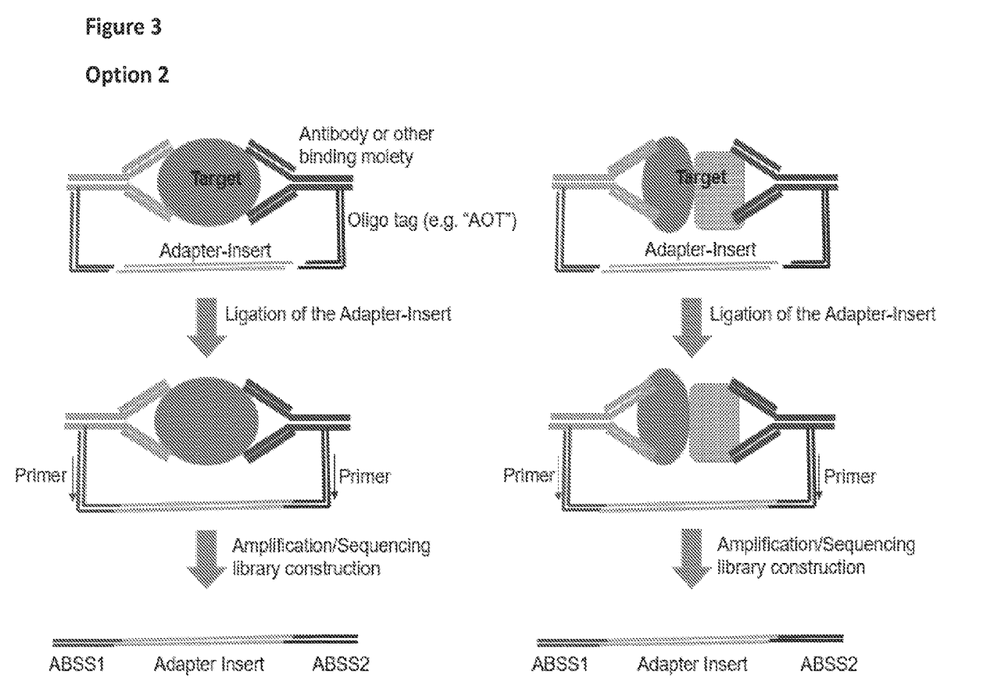
FIG. 3 is a flowchart illustrating the compounds and methods of the present invention for detecting and measuring closer protein-protein interactions and identification of multiple proteins and their modifications. In this embodiment, the DNA Product is shorter than that shown in FIGS. 1 and 2, and it is directly amplified for analysis.

There are two design approaches that differ in length of the resulting DNA Product: "Option 1" (if the distance between the antibodies is more than about 60 nm)—A long DNA Product that is subsequently self-ligated; and "Option 2" (if the distance between the antibodies is less than about 60 nm)—A short DNA Product which is directly amplified for analysis. The length of the resulting DNA Product can be controlled by varying the length of either the Adapter-Insert or the AOTs, or both. Option 1 is particularly well suited for detecting and quantifying interactions between and within large complexes, organelles, and cells, and measuring distances between organelles and cell sub-structures (FIG. 1-2). Option 2 is particularly effective at detecting and measuring protein-protein and macro-molecular interactions, and the identification of multiple proteins and their modifications (FIG. 3).

Option 1 (FIG. 1). Detecting distant interactions between or within large complexes. Large complexes may have dozens of proteins in a complex. It is possible to choose the length of the Adapter-Insert plus AOTs to allow interactions between antibodies bound to proteins within the complexes that are located relatively far apart in these large structures. An average diameter of a protein of 50 kDa is about 5-7 nm. Diameter of an antibody molecule is 10-15 nm. Length of the AOT is 0.7 nm per base. In order to be able to detect proteins in a complex consisting of tens of protein molecules (e.g. nuclear pore complexes, or ribosome) an Adapter-Insert plus AOTs should be sufficiently long, so that the resulting ligated DNA Product would cover the distance between targets in this complex. In one embodiment, long range interactions (about 60 nm and more) can be quantitatively/semi-quantitatively analyzed. The length of the Adapter-Insert plus AOTs is chosen to fit the distance between proteins in the structures or within the structure. Option 1 DNA Product (comprising the AOTs and the Adapter-Insert) is preferably between about 60 nm and 10 um in length, more preferably between about 120 nm and 1000 nm, and most preferably between about 140 nm and 500 nm.

Pairs of antibodies against proteins of interest are chosen. Each of the antibodies is conjugated to an AOT with a sequence that contains a restriction site proximal to the connection to the antibody molecule followed by the ABSS at the distal end. When the conjugated antibodies have specifically bound to their target(s), the AOTs are ligated together using an Adapter-Insert, forming a "DNA Product" (AOT of Ab1 ligated to the Adapter-Insert, which is also ligated to AOT of Ab2). The DNA Product, or a portion thereof, is cleaved off from the antibodies by the restriction enzyme ("RE"), which is subsequently inactivated. The DNA Product, or a portion thereof, is self-ligated by intra-molecular ligation so that the ABSSs will come to be in proximity to each other. The DNA sequence including two ligated ABSSs within the AOTs is amplified via PCR with primers corresponding to sequences located in the flanking sections of the Adapter-Insert (FIG. 1-2). The resulting DNA product can be detected using any DNA detection method such as NGS, qPCR, digital PCR or branching DNA detection. If detection is done using NGS, the DNA product sequence optimally should not exceed 100 nt. During the above PCR step, primers for NGS sequencing can be attached and the sequencing library is prepared. Sample bar-codes for pulling different samples into one NGS run can also be attached at this stage. In embodiments where NGS is used, any platform for NGS sequencing may be used. Ion Torrent or Illumina are the preferred NGS platforms. Thus the library construction should be carried out according to the specifications of the NGS platform to be used. Depending on the specific structure of the DNA components the output data file will contain multiple sequence reads that correspond to the ABSSs, specifically a single read may contain nucleotide sequence that corresponds to common sequence 1, followed by ABSS of Ab1, followed by Adapter-Insert, followed by the reverse sequence of ABSS of Ab2 and then common sequence 2. There will be multiple reads corresponding to each ABSS pair. The number of reads corresponds to the number of ABSS pairs.

Another way to detach the DNA Product from the antibody-antigen complexes, is to have the attachment chemistry in the internal part of the AOT for conjugation to antibodies (not on the end). In this case both ends of the AOT will be free to ligate—one end to Adapter-Insert, the second to self-ligate the DNA Product or a portion thereof. To facilitate, for conjugation, one can use an attachment chemistry that enables cleavability. In this case, after formation of antibody-antigen complexes and subsequent ligation of the Adapter-Insert, one can cleave off (via cleavable attachment chemistry) the DNA Product, or a portion thereof, from the antibody-antigen complexes.

The resulting DNA sequence optimally should not exceed 100 nt. During this PCR step, primers for NGS or other sequencing are attached. Sample bar-codes for pulling different samples into one NGS run can also be attached at this stage.

Option 1 can also be used for analysis of cell-cell interactions, for example interaction of multiple host cell types in tumor sections (FIG. 2). This application appears to be quite unique and useful. For studies of interactions between different cells, both cytoplasmic and membrane-associated antigens can be used, such as membrane proteins or their interacting partners. This method can also be used for studies of positioning of organelles or subcellular structures relative to each other, or re-localization of proteins to specific locations within a cell. Currently such studies are done using microscopy, which is very useful for qualitative assessments but does not readily support quantitative measurements. To study these interactions, the method is best used with fixed cell or tissue preparations.

Distances between organelles or subcellular structures can also be measured with Option 1 by using a series of barcoded Adapter-Insert molecules plus AOTs of different lengths. Representative organelles or subcellular structures that can be analyzed include, but are not limited to, mitochondria, ER, cellular membrane, nucleus, nucleolus, Golgi, lysosomes, vacuole, chloroplast, ribosomes, and nuclear pore complexes. In one embodiment the cells are preferably fixed, permeabilized and treated with an antibody-conjugate mix. The Adapter-Inserts are added into a ligation mix. AOTs are ligated to the Adapter-Inserts. The resulting DNA Product molecules are cut off of the antibodies using the restriction enzyme and self-ligated. The ABSS portion of the ligated AOT pairs are amplified with primers in the Adapter-Insert. Adapter-Inserts plus AOTs that are too short will not produce products for sequencing, and increasing the length will allow generation of more products until the plateau is reached, indicating the distance between the targets of interest.

Option 2 (FIG. 3). Detecting close protein-protein and macro-molecular interactions and individual proteins and their modifications. A shorter DNA Product is optimal. In this embodiment, shorter range interactions up to 100 nm apart can be quantitatively/semi-quantitatively analyzed. The length of the Adapter-Insert plus AOTs is chosen to fit the distance of the interactions being analyzed.

In this Option 2, the AOT for each antibody should be designed such that its ABSS is on the distal end and its common sequences should be located close to the antibody molecule with which it is conjugated.

After the ligation of the Adapter-Insert to both AOTs, each conjugated to a member of the pair of antibodies bound to their specific target(s), the DNA Product, or a portion thereof, is amplified using primers against either common sequences I and II or ABSS sequences. The resulting DNA sequence should not exceed 100 nt for efficient subsequent sequencing analysis. In one embodiment, NGS sequencing is preferred. During this step the PCR primers for NGS sequencing are attached. Sample bar-codes for pulling different samples into one NGS run can also be attached at this stage.

MDISA Option 2 can be used for detection, identification and quantitation of individual proteins or their post-translational modifications in a highly multiplexed format.

When identifying individual proteins or their modifications (as in Option 2), cross-reactivity will be minimized because i) only ligated AOT pairs will be selected for PCR amplification and thus show up in the sequencing results; and ii) the AOTs conjugated to the antibody pair that are in proximity with each other will preferentially generate one product for detection and analysis. If the sequence read contains a ligated pair of 'mismatched' AOTs (for two antibodies, each specific for different targets) this will indicate that both of these targets are located in one complex. Thus complex analysis can be performed in the same reaction as individual protein quantification by including antibodies that can interact in parallel with each other with the same target or targets within the same complex.

If necessary to reduce the background, antibodies unbound to their targets can be removed. Any method known in the art for such removal can be used, including, but not limited to the use of a solid support to pull out the components of the sample with bound antibodies. In one embodiment, components of the sample can be bound to a solid support, e.g. by biotinilating the lysate. In this case the antibody mix is incubated with a biotinilated lysate which is subsequently isolated with Streptavidin beads. Below are several examples of detection methods in accordance with the present invention.

EXAMPLE 1

Identifying Proteins in a Protein Complex

In one example, we measured association of GFP protein with a mutation in the stop codon (non-stop GFP) with another protein Bag3. The interaction takes place on a large ribosome subunit, and there could be a significant distance between non-stop GFP and Bag3 proteins (tens of nanometers) due to the geometry of the ribosome subunit. Therefore, to measure the interaction, we utilized the MDISA method. As predicted based on prior studies, possible interaction between non-stop GFP and Bag3 should be stimulated by a compound MG. HeLa cells were transfected with plasmids expressing non-stop GFP and FLAG-tagged Bag3 and treated with MG or left untreated. As controls, HeLa cells were transfected with non-stop GFP only (sample MG-GFP) or Flag-tagged Bag3 (sample MG-Bag3) only. Cells were plated on wells of 96-well plate (either 1000 or 300 cells per well). Cells were fixed and incubated with primary antibodies against GFP and FLAG, according to our protocol. Then secondary antibodies conjugated with oligos were incubated with the samples and extensively washed. DNA ligase was added to the mixture to ligate AOT1, Adapter Insert and AOT2 to create triple AOT1-Adapter Insert-AOT2 DNA product. The samples were washed again to remove the non-ligated adapter inserts. The ligated triple DNA product was amplified by qPCR using primers that bind to the ABSS1 and ABSS2.

Figure 5:
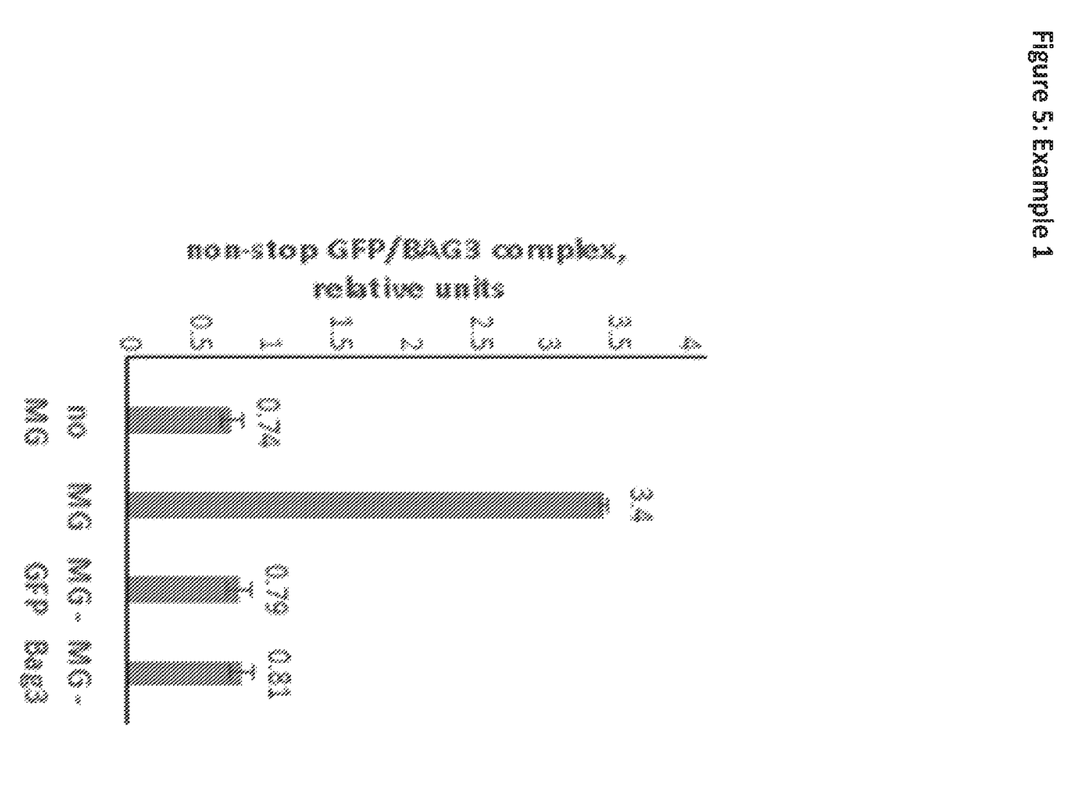
FIG. 5 illustrates the association of non-stop GFP with Bag3 measured by the MDISA method of the present invention. Incubation with MG strongly enhances the association. The right two columns are negative controls without expression of either nsGFP or Bag3.
Figure 6A:
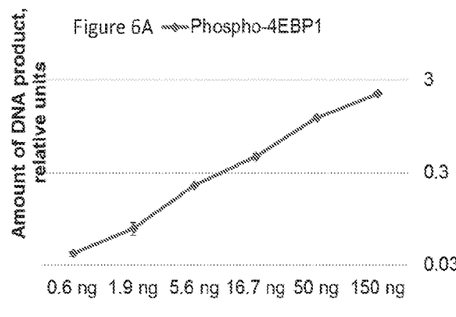
FIG. 6A illustrates detection of Target A, which is phospho-4EBP1.
Figure 6B:
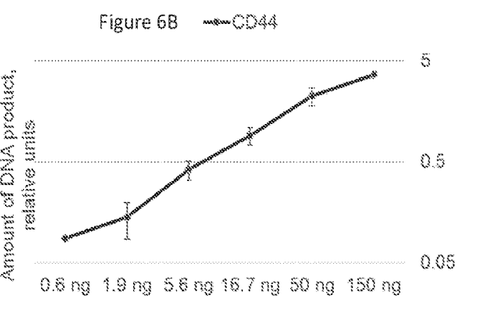
FIG. 6B illustrates detection of Target B, which is CD44.
Figure 6C:
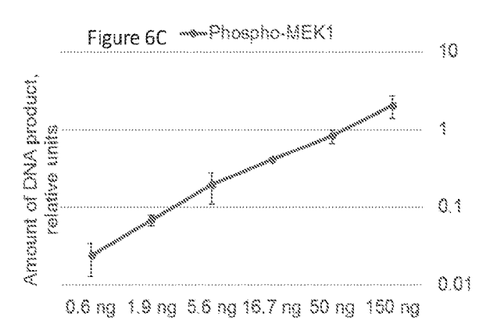
FIG. 6C illustrates detection of Target C, which is phospho-Mek1.
Figure 6D:
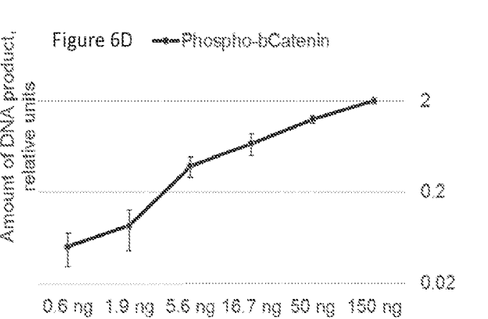
FIG. 6D illustrates detection of Target D, which is phospho-beta Catenin.
Figure 6E:
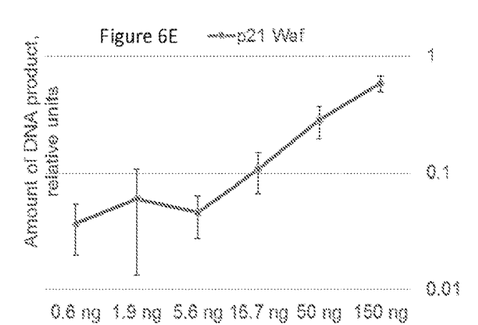
FIG. 6E illustrates detection of Target E, which is p21Waf1.
Figure 6F:
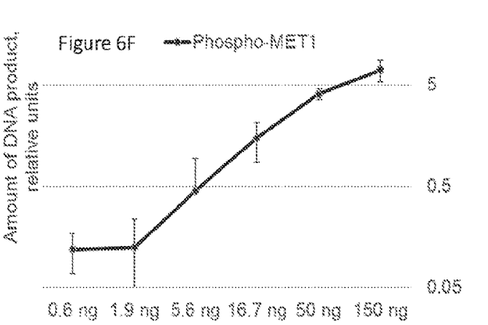
FIG. 6F illustrates detection of Target F, which is phospho-Met1.

Detection of the association of non-stop GFP with Bag3 measured by the MDISA method is demonstrated by the graph as shown in FIG. 5. As demonstrated by the results shown, incubation with MG strongly enhances the association. In the graph shown in FIG. 5, the right two columns are negative controls without expression of either nsGFP or Bag3.

EXAMPLE 2

Detecting Several Proteins of Interest

MDISA was used to detect several proteins of interest. To define sensitivity and dynamic range of the assay, cell lysate was titrated in the range between 0.6 ng and 150 ng and measured the content for several selected targets. As seen in the FIGS. 6A-6F, in most cases there is a clear linearity in the range between 5.6 ng to 150 ng and for some targets the dynamic range is even wider. In the graphs in FIGS. 6A-6F, the Y-axis is the relative amount of DNA product (relative to the 150 ng datapoint, which is equal to 1).

EXAMPLE 3

Multiplex Protein Detection

The present assay can be used to detect multiple analytes simultaneously in a single sample. Expression level, phosphorylation and cleavage of a large number of proteins can be detected. The samples can be cell/tissue lysates, biopsies, or other types of samples. In this example, samples A and B were compared using the MDISA method of the present invention. The assay was performed to detect the level of 70 different analytes in each of Sample A and B.

The data was generated based on three repeats for each sample, and where sample A values for each target are normalized to 1. Sample A was obtained from HeLa cell line and Sample B was obtained from HCT116 cell line. After the samples are obtained, the samples are blocked with a blocking buffer and incubated with a mix of analyte-binding moieties against all 70 targets. In this case analyte-binding moieties are antibodies. There are a pair of antibodies per target. Each antibody pair consists of (1) antibody 1 against an epitope on protein X, conjugated to a 5' Thiol of double-stranded DNA oligo tag (30 bp) with a sticky end on the 3'-end; (2) antibody 2 against another epitope on protein X, conjugated to a 5' Thiol of double-stranded DNA oligo tag (30 bp) with a sticky end on the 3'-end. The sticky ends on antibodies 1 and 2 are not complementary and cannot ligate to each other.

The incubation mixture is extensively washed to remove non-bound antibodies, and a mixture of double-stranded adapter inserts (20 bp) with sticky ends, complementary to the DNA oligo tags on antibodies 1 and 2, are added to the samples. We add DNA ligase to ligate AOT1, Adapter Insert and AOT2 of antibody pairs of all 70 targets to create triple AOT1—Adapter Insert—AOT2 DNA products. The sample is washed again to remove the non-ligated adapter inserts. The ligated DNA products are amplified by PCR. Digital qPCR platform Fluidigm Biomark was used to quantify the amount of the ligated triple DNA products in different comparison samples. The amount of these products reflects the presence of a target protein (its modification or cleavage product). Primers that bind to the ABSS1 and ABSS2 of individual antibody pairs were used for digital qPCR platform Fluidigm Biomark.

Figure 7:
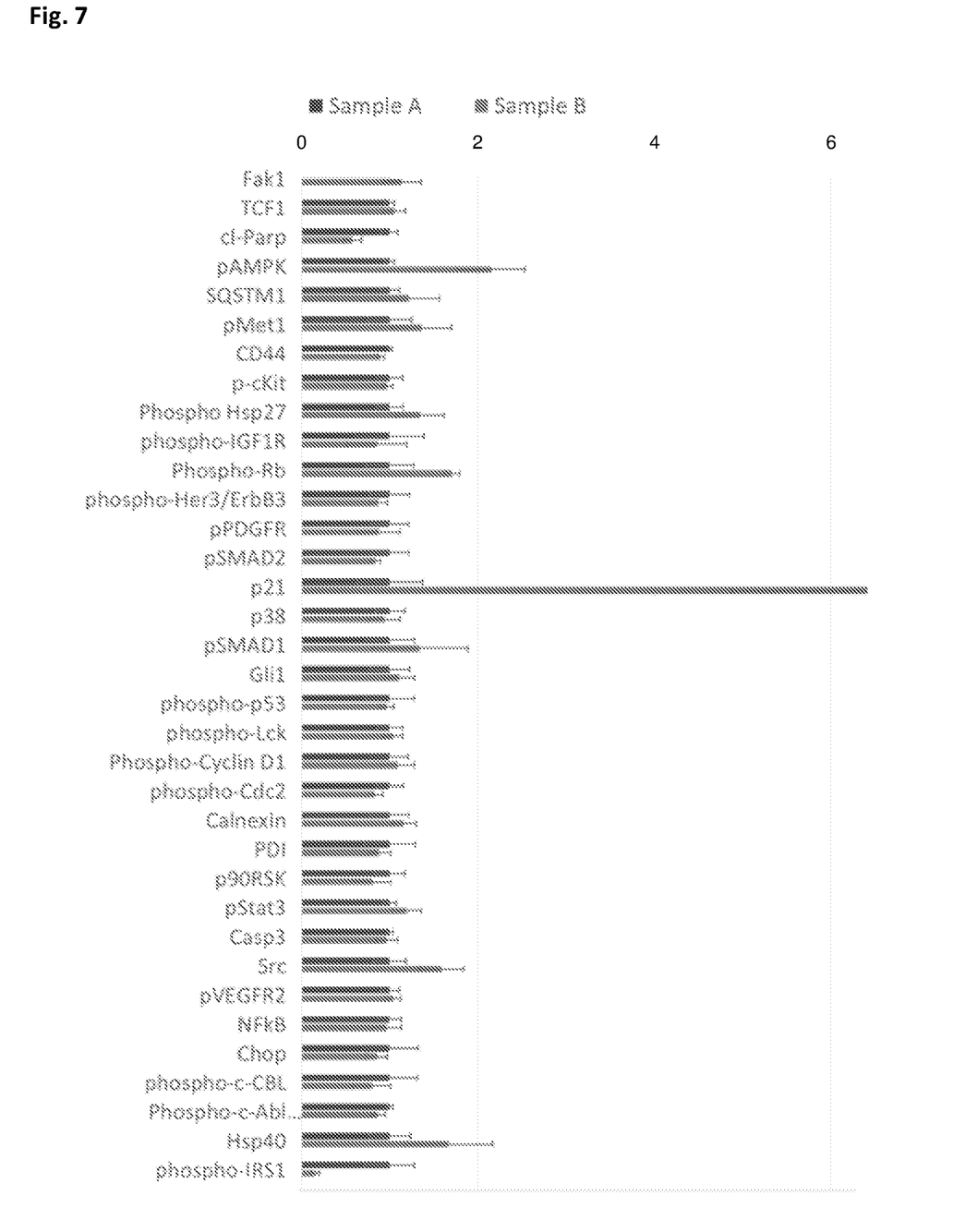
FIG. 7 illustrates the amount of 70 proteins detected in each of two samples by the MDISA method of the present invention. The amount of proteins detected in Samples A and B are shown.

The results are shown in the graph in FIG. 7, which illustrates the amount of each protein detected in each sample by the assay of the present invention. The amount of proteins detected in Sample A are shown in blue and the amount of proteins detected in Sample B are shown in orange. As an example, the amount of FAK1 protein detected in Samples A and B are very similar; the amount of pAMPK detected in sample B is about twice as much as detected in sample A; and the amount of p21 detected in sample B is about six times as much as detected in sample A.

While the invention has been particularly shown and described with reference to certain embodiments, it will be understood by those skilled in the art that various changes in form and detail may be made without departing from the spirit and scope of the invention. The scope of the invention should be determined, therefore, only by the following claims.

The invention claimed is:

1. A method for detecting analytes and association between analytes in a sample, the method comprising:
   a) incubating the sample with at least two analyte-binding moieties that each carry a double-stranded DNA oligo tag specific for each binding moiety, wherein the double-stranded DNA oligo tags are not able to ligate to each other;
   b) adding to the components from step (a) at least one double-stranded adapter-insert DNA molecule, wherein the opposing ends of the double-stranded adapter-insert DNA molecule can ligate to the double-stranded DNA oligo tags of the binding moieties;
   c) adding a ligase to the mixture from step (b), resulting in a ligated single DNA product comprised of the double-stranded DNA oligo tags, and the double-stranded adapter-insert DNA, attached to the analyte-binding moieties, wherein the adapter-insert is ligated between the oligo tags, and the ligated single DNA product is double-stranded;
   d) detecting the ligated single DNA product from step (c), or a portion or portions thereof; and
   e) analyzing the detected DNA product or a portion or portions thereof from step (d), to identify and quantitate analytes and associations between analytes.

2. The method of claim 1, further comprising the following steps in between steps c and d:
   i) detaching the ligated DNA product, or a portion thereof, from the binding moieties, and
   ii) self-ligating the DNA product, or a portion thereof, wherein the DNA oligo tags, or portions thereof, are located in proximity to each other.

3. The method of claim 1, wherein the binding moieties are selected from the group consisting of antibodies, Fab fragments, single chain antibodies, modifications of recombinant antibodies or their fragments, any derivatives of antibody display libraries, aptamers and alternative scaffolds.

4. The method of claim 1, wherein multiple analytes are detected in a mix.

5. The method of claim 1, wherein the analyte is selected from the group consisting of individual proteins, protein complexes, cellular components, sub-cellular structures, protein modifications, and DNA or RNA modifications.

6. The method of claim 5, where the analyte is from an organism selected from the group consisting of bacteria, fungi, humans, plants, and non-human animals.

7. The method of claim 1, wherein the sample is selected from the group consisting of tissue samples, tumor biopsies, cells in culture, biological fluids, blood, plasma, serum, cell lysates, fine needle biopsies, micro-dialysis fluid, cell culture media, dried blood spots, synovial fluid, cerebrospinal fluid, plaque extract, saliva, urine, frozen sample, FFPE samples, and intact fixed cells.

8. The method of claim 1, wherein the analyte is bound to a solid support.

9. The method of claim 1, wherein one or more of the binding moieties is bound to a solid support.

10. The method of claim 1, wherein the analytes or association between analytes being detected are greater than 60 nm apart from each other.

11. The method of claim 1, wherein the association between analytes being detected are selected from the group consisting of interactions between different cells or cell types (cell-cell interactions), organelles or subcellular structures.

12. The method of claim 11, wherein distances between different organelles or subcellular structures are measured using a series of adapter-inserts of different length in the ligation reaction.

13. The method of claim 1, wherein the adapter-insert is unique for each of the at least two analyte-binding moieties.

14. The method of claim 1, wherein the oligo tag comprises an antibody signature sequence (ABSS).

15. The method of claim 14, wherein the oligo tag further comprises a common sequence.

16. The method of claim 1, wherein the analyzing of the sequences in step (e) is performed by a method selected from the group consisting of qPCR, next generation sequencing, digital PCR, and branching DNA.

17. The method of claim 1, wherein the adapter-insert is common for all the analyte-binding moieties.

18. The method of claim 1, wherein the adapter-insert is common for a sub-set of the analyte-binding moieties.

19. A method for detecting analytes and association between analytes in a sample, the method comprising:
   a) incubating the sample with at least two primary analyte-binding moieties and at least two secondary analyte-binding moieties, wherein the primary analyte-binding moieties bind the analyte and the secondary analyte-binding moieties bind the primary analyte-binding moieties, wherein the secondary analyte-binding moieties carry double-stranded DNA oligo tags specific for each binding moiety, wherein the double-stranded DNA oligo tags are not able to ligate to each other;
   b) adding to the components from step (a) at least one double-stranded adapter-insert DNA molecule, wherein the opposing ends of the double-stranded adapter-insert DNA molecule can ligate to the double-stranded DNA oligo tags of the binding moieties;
   c) adding a ligase to the mixture from step (b), resulting in a ligated single DNA product comprised of the double-stranded DNA oligo tags, and the double-stranded adapter-insert DNA, attached to the secondary analyte-binding moieties, wherein the adapter-insert is ligated between the oligo tags, and the ligated single DNA product is double-stranded;
   d) detecting the ligated single DNA product from step (c), or a portion or portions thereof; and
   e) analyzing the detected DNA product or a portion or portions thereof from step (d) to identify and quantitate analytes and associations between analytes.

* * * * *